(12) United States Patent
Koga et al.

(10) Patent No.: US 7,034,191 B2
(45) Date of Patent: Apr. 25, 2006

(54) CONTINUOUS CRYSTALLIZATION PROCESS

(75) Inventors: Yoshio Koga, Ibaraki (JP); Hiroaki Kimura, Ibaraki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/057,372

(22) Filed: Feb. 15, 2005

(65) Prior Publication Data

US 2005/0159631 A1    Jul. 21, 2005

Related U.S. Application Data

(63) Continuation of application No. PCT/JP03/12076, filed on Sep. 22, 2003.

(30) Foreign Application Priority Data

Oct. 28, 2002    (JP) .............................. 2002-312256

(51) Int. Cl.
*C07L 37/68*    (2006.01)

(52) U.S. Cl. ................................... 568/724

(58) Field of Classification Search ................. 568/724
See application file for complete search history.

(56) References Cited

U.S. PATENT DOCUMENTS

| 4,927,978 | A | * | 5/1990 | Buechele et al. | ............ 568/724 |
| 4,950,805 | A | * | 8/1990 | Iimuro et al. | ............... 568/724 |
| 5,345,000 | A | * | 9/1994 | Moriya et al. | ............... 568/722 |
| 6,806,394 | B1 | * | 10/2004 | Evitt et al. | ................... 568/728 |

FOREIGN PATENT DOCUMENTS

| EP | 0 332 203 | 9/1989 |
| EP | 0 522 700 A2 | 1/1993 |
| EP | 0 558 214 | 9/1993 |
| WO | WO 91/05755 | 5/1991 |
| WO | WO 200240435 A1 * | 5/2002 |

* cited by examiner

*Primary Examiner*—Michael L. Shippen
(74) *Attorney, Agent, or Firm*—Nixon & Vanderhye P.C.

(57) ABSTRACT

A continuous crystallization process comprising the steps of supplying a crystallization material containing bisphenol A to a crystallizer to form crystals of an adduct of bisphenol A and phenol or crystals of bisphenol A, subjecting the slurry discharged from the crystallizer to solid/liquid separation, and recovering the crystals, wherein part of the mother liquor is circulated to the crystallizer. According to this process, the heat duty to be removed is reduced, deposition of solids on the inner surfaces of the crystallizer, particularly on the heat transferring surface of the cooler is restrained, and consequently the continuous operating time of the apparatus is prolonged.

6 Claims, 2 Drawing Sheets

CONTINUOUS CRYSTALLIZATION PROCESS

This is a continuation application of International Application PCT/JP2003/12076 filed Sep. 22, 2003. The entire content of this application is incorporated herein by reference.

TECHNICAL FIELD

The present invention relates to an improved continuous crystallization process. More particularly, it relates to an improved process for continuously forming the crystals of bisphenol A and phenol adducts or the crystals of bisphenol A.

BACKGROUND ART

It is known to produce bisphenol A by reacting an excess amount of phenol with acetone in the presence of an acid catalyst. As the method for obtaining high-purity bisphenol A from the above reaction product, a method is known in which the reaction product is subjected to a crystallization treatment to precipitate the crystals of an adduct of bisphenol A and phenol (hereinafter referred to as "adduct crystals"), then a slurry of the obtained crystals is subjected to solid/liquid separation, and the phenol is removed from the recovered adduct crystals. In another method, bisphenol A crystals are precipitated instead of adduct crystals.

A continuous crystallization process is known as a method for purifying a large volume of crude material at high efficiency. In carrying out continuous crystallization, usually concentration of material is adjusted in the material preparation step, and the material is supplied to a crystallizer after the temperature has been adjusted to a degree not lower than the saturation temperature. In this case, an excess rise of temperature of the material leads to an increase of the quantity of the required heat in the crystallizer. This, in turn, duty of cooling the supersaturation, which not only induces an increased rate of nucleation to reduce the average size of crystals, but also encourages deposition of scale on the heat transferring surface of the cooler, the inner surfaces of the pipes, etc. Therefore, in the material-to-be-crystallized (hereinafter referred to as crystallization material) preparation step, usually the temperature is adjusted to a degree which is slightly (such as +3° C.) above the saturation temperature.

As a continuous crystallization process of adduct crystals, a method is known comprising the steps of crystallization, solid/liquid separation, washing and crystal re-dissolving with a plural number of (1st to (n-1)st) stages, in which (a) purified phenol is used as the washing liquid for the crystals obtained at the n-th stage, (b) the washings or mother liquor recovered at the n-th stage is used as the phenol solution for re-dissolving the crystals obtained at the n-1th stage, (c) the mother liquor or washings recovered at the n-th stage is used as the washing liquid for the crystals obtained at the n-1th stage, and (d) the concentration of impurities in the phenol solution for re-dissolving the crystals and the concentration of impurities in the washing liquid of the crystal at each of the 1st to n-1th stages are made higher than those at the succeeding stage (Japanese Patent Application Laid-Open (KOKAI) No. 5-117194).

However, according to the studies by the present inventors, it was found that the proposal in the above-mentioned patent to use the mother liquor exclusively for the dissolution of crystals as a way of effective utilization of the mother liquor in the crystallization process has the problem that the crystals tend to precipitate on the heat transferring surface of the cooler, the inner surfaces of the pipes, etc., to form a deposit called scale, jeopardizing the long-time stable operation of the apparatus. Particularly in the case of a crystallization apparatus having an external circulation type cooling system, the scale tends to deposit on the heat transferring surface of the cooler, the inner surfaces of the pipes located downstream of the meeting point of the crystallization material and the coolant slurry, and other parts to make it difficult or even unable to carry on the continuous long-time stable operation of the apparatus.

The present invention has been made in view of the above circumstances, and its object is to provide an improved continuous crystallization process which can be applied to continuous formation of adduct crystals or bisphenol A crystals, according to which the heat duty that needs to be removed in the crystallization operation is lessened and the solid deposition on the inner surfaces of the crystallizer, especially on the heat transferring surface of the cooler, is restrained to allow prolongation of the continuous operation period of the crystallizer.

DISCLOSURE OF THE INVENTION

Figure 1:
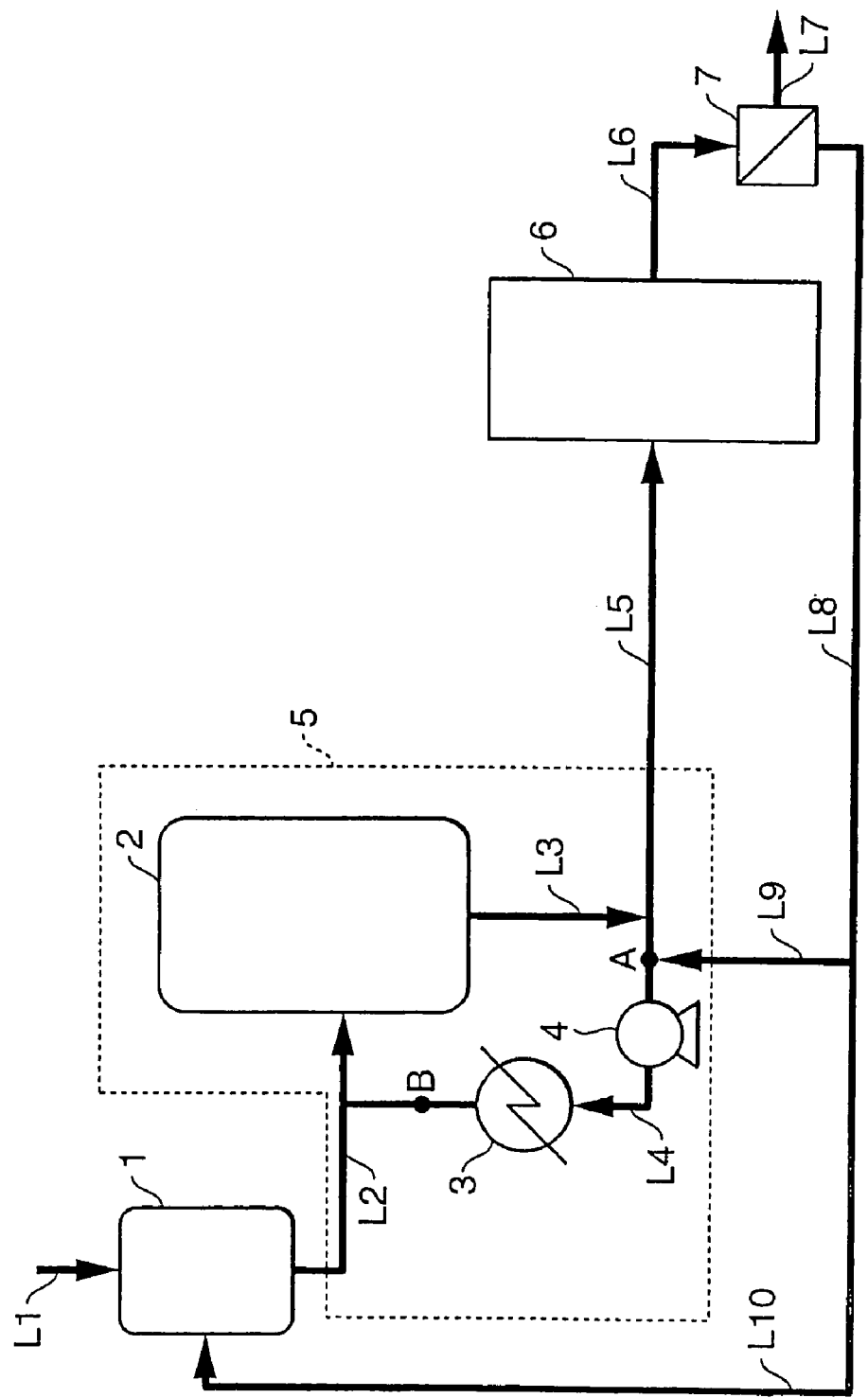
FIG. 1 is an example of process flow sheet for carrying out the process of the present invention.

As a result of the present inventors' earnest studies on the subject matter, the following findings has been found. In making effective utilization of the mother liquor in the crystallization process, it is advantageous to let part of the mother liquor circulate in the crystallizer because, in this case, the crystallizer is kept from being exposed to useless heating which is unavoidable in case where the mother liquor is circulated to the crystallization material preparation tank, and thereby it is possible to lessen the heat duty that needs to be removed in the crystallization operation. It is further possible to suppress the generation of deposition (namely, the generation of scale) by an amount corresponding to the reduction of enthalpy (or temperature) of the crystallization material made possible by avoiding useless heating. Of course, the obtained crystals remain unaffected at all in their quality even when the mother liquor is circulated to the crystallization material preparation tank without circulating it to the crystallizer.

The present invention has been attained on the basis of the above finding, in an aspect of the present invention, there is provided an improved continuous crystallization process comprising the steps of supplying a crystallization material containing bisphenol A to a crystallizer to form the crystals of an adduct of bisphenol A and phenol or the crystals of bisphenol A, subjecting the slurry discharged from the crystallizer to solid/liquid separation, and separating the crystals from the mother liquor, with part of the mother liquor being circulated to the crystallizer.

The invention will be described in detail hereinafter with reference to its embodiments. The crystallization process of the present invention comprises basically a crystallization material preparation step, a crystallization step and a solid/liquid separation step.

In the crystallization material preparation step, a material to be crystallized, for example, a phenol (hereinafter referred to as PL) solution of bisphenol A (hereinafter referred to as BPA) and the mother liquor circulated from the solid/liquid separation step are supplied to a crystallization material preparation tank to prepare the crystallization material. As the PL solution of BPA, usually the reaction product obtained from an acetone and PL reaction step is used, and if necessary, the BPA concentration may be adjusted by evaporating part of the solution or by adding the circulated mother liquor, or the solution may be heated by utilizing a heat exchanger to dissolve the crystals. Further, the crystals obtained from the preceding crystallization step, after solid/liquid separation, may be mixed with the circulated mother liquor or heated to obtain the desired crystallization material adjusted in BPA concentration and temperature.

The temperature for the crystallization material preparation step (tank) is usually set at a degree which is higher than the saturation temperature of the PL solution of BPA. Its preferred temperature is 1 to 10° C., more preferably 1 to 5° C. higher than the saturation temperature. The above saturation temperature can be determined, for example, by referring to the saturation solubility curves described in the known literature, e.g. Japanese Patent Application Laid-Open (KOKAI) No. 5-15701, after specifying the BPA concentration by gas chromatography or near infrared ray analysis.

In the material preparation tank, the solution is preferably agitated by using an agitator to homogenize the solution. In case of conducting liquid/liquid mixing at the material preparation stage, a static mixer or like means may be used.

In case of precipitating the adduct crystals, the crystallization material prepared in the material preparation tank is a PL solution or aqueous solution of BPA with a BPA concentration of usually 18 to 50% by weight, preferably 22 to 30% by weight. It may be a mixed solvent containing either of acetone, water and PL. The PL solution may be a slurry containing a slight quantity of solids, but preferably it is a perfect solution for the benefit of re-crystallization. The temperature of the crystallization material is usually 60 to 120° C.

In the crystallization step, the crystallization material supplied into the crystallizer is cooled there or concentrated by the evaporation of the solvent, and the crystals are precipitated to form a slurry. As the crystallizer, there can be used, for instance, an internal cooling type crystallization tank or a crystallization tank having an external circulation type cooling system. The crystallization tank having an external circulation type cooling system is preferably used for the reason that the slurry flow is relatively definite. In a preferred form of the external circulation cooling type crystallizer, there are provided a crystallization tank and an external circulation line having an external cooler, and the crystallization material is supplied to the tank after mixed with the slurry discharged from the external cooler.

For instance, when adduct crystallization is carried out by using an external circulation cooling type crystallizer, the crystallization material is mixed with the circulated slurry cooled in the external circulation line, and is thereby cooled to 45 to 65° C. and then supplied to the crystallization tank. Usually, the crystallization tank has a heat-insulating structure. The process fluid passing the crystallization tank undergoes a slight degree of heat generation as a consequence of crystallization, so that there exists a temperature difference of usually 0 to 3° C. between the inlet and the outlet of the crystallization tank.

In the present invention, temperature difference between the crystallization material at the outlet of the crystallization material preparation tank and the slurry at the outlet of the crystallization tank is usually 5 to 35° C., preferably 10 to 20° C.

The slurry discharged from the crystallization tank is partly supplied to the solid/liquid separation step while the other portion is supplied to the external circulation line provided with an external cooler. The ratio of the portion of the slurry supplied to the solid/liquid separation step is decided primarily with the condition of crystallization in the crystallization tank as an index. This ratio is usually 1 to 30% by weight, preferably 1 to 10% by weight.

In the crystallization step, it is more effective to use a plural-stage crystallization tank. When, for instance, a two-stage crystallization tank is used, a higher crystallization effect than obtainable with a single-stage tank can be obtained as the temperature of the circulating mother liquor after solid/liquid separation becomes lower than the temperature of the first stage tank. The number of the crystallization tanks to be installed in the crystallization step is not specifically defined, but it is usually 1 to 3. The crystallizer may be provided with a heater for dissolving the crystallites to enlarge the average grain size of the crystals.

In the solid/liquid separation step, the slurry is supplied into a solid/liquid separator and separated into crystals and mother liquor. In case where the solids are washed in the separator, the washings are treated as mother liquor. In the case of crystallization of an adduct, the temperature of the mother liquor discharged from the separator is usually 65 to 45° C.

The process of the present invention features that the mother liquor discharged from the separator is partly circulated to the crystallizer. In the following description, the portion of the mother liquor circulated to the crystallizer is called circulated mother liquor.

The circulated mother liquor is preferably temporarily kept in a container, with the residence time being usually not longer than 10 minutes. The crystallization slurry to which the said mother liquor is circulated has a viscosity of usually not higher than 20 cP. The mother liquor is almost saturated, so that there is a possibility that precipitation of crystals would take place in the circulation piping. Therefore, the container and the circulation pipes are preferably designed to be able to maintain a temperature by insulation or heating. Excessive heating, however, spoils the effect of lessening the heat duty that needs to be removed, so that the temperature of the mother liquor should preferably be kept at saturation temperature minus 1 to 3° C.

The mother liquor preferably contains a small quantity of fine crystals (the crystals that leaked out from the solid/liquid separator). This is for the reason that when the pipes were overheated, the crystals would be dissolved to help the mother liquor maintain saturation. On the other hand, even if the mother liquor is cooled by heat dissipation or other causes and brought into an oversaturated state, it shows a strong tendency to promote growth of the crystals, so that scaling on the circulation pipes is retarded to some extent. The content of such crystallites, when expressed in terms of concentration at the outlet of the solid/liquid separator, is usually 0.01 to 10% by weight, preferably 0.1 to 5% by weight.

The mother liquor is directly circulated to the crystallizer. In the case of, for instance, an external circulation cooling type crystallization tank, the mother liquor circulated to the crystallization step is supplied to either: (1) a point between the outlet of the crystallization material preparation tank and its junction with the external circulation cooling line, or a point between the said junction and the crystallization tank;

(2) the line from the crystallization tank to the external cooler; or (3) a point between the outlet of the external cooler and the said junction.

In case where a cooler is provided in the crystallization tank, or in the case of an evaporation cooling type crystallizer, direct circulation of the mother liquor into the crystallization tank is more advantageous as it provides a greater reduction of the heat duty to be removed. In this case, it is preferable that the mother liquor supply point is distant from both the outlet of the crystallization tank and the crystallization material feed port.

The circulation rate of the mother liquor to the crystallizer is usually 5 to 60% by weight, preferably 10 to 50% by weight, based on the slurry discharge from the crystallizer. Also, in the present invention, part of the mother liquor may be circulated to the crystallization material preparation step within limits not prejudicial to the effect of the invention. The crystallization material preparation step in the first-stage crystallization process is a reaction step. In this case, the ratio of the amount of mother liquor (A) circulated to the crystallizer to the amount of mother liquor (B) circulated to the crystallization material preparation tank, B/A, is usually not more than 5, preferably not more than 3, even more preferably not more than 2.

According to the process of the present invention, it is possible to substantially reduce the heat duty to be removed in the cooler. It is further possible to lessen the total amount of heat duty required per kg of the product.

The effect of the process of the present invention can be determined with the degree of supersaturation of BPA as a measure. Here, the degree of supersaturation can be expressed by the formula: (X−Xsat)/Xsat where X is weight fraction of BPA in the solution, and Xsat is weight fraction of BPA in the saturated solution at the measuring temperature of the said solution. It is very important to control the degree of supersaturation as the primary nucleus generation rate and the scale growth rate in the solution rise exponentially against the degree of supersaturation. In I&EC Process Design and Development (1964), Vol. 3, No. 4, the relation between the degree of supersaturation or the heat duty to be removed and scaling on the heat transferring surface is formulated, suggesting that scaling can be controlled if the degree of supersaturation and the heat duty to be removed are lessened.

According to the process of the present invention, it is possible to lower the degree of supersaturation at the locations where the degree of supersaturation would rise excessively with the prior art, particularly at the heat transferring surface of the cooler and the vicinity thereof. More specifically, in the crystallizer, there takes place local overcooling at the spot where the mother liquor is circulated, causing a rise of the degree of supersaturation even if no cooling is made to promote the precipitation of crystals. Consequently, the heat duty that needs to be removed is lessened to reduce the degree of supersaturation, particularly at the heat transferring surface and the vicinity thereof. Thus, since the temperature variance at the heat transferring surface of the cooler can be reduced, scaling on such heat transferring surface can be controlled, which greatly contributes to the long-time stabilization of the crystallizer operation.

To put it in a more concrete way, (1) if the spot to which the mother liquor is circulated is between the outlet of the material preparation tank and the junction with the external circulation cooling line, the degree of supersaturation of the whole crystallizer is lowered; (2) if the said spot is between the said junction and the crystallization tank, the degree of supersaturation in the section from the external cooler to the said junction is lowered; (3) if the mother liquor is circulated to the line from the crystallization tank to the external cooler, the degree of supersaturation in the section from the external cooler to the said junction is lowered; and (4) if the said location is between the outlet of the external cooler and the said junction, the degree of supersaturation in the section from the external cooler to the said junction is reduced.

BEST MODE FOR CARRYING OUT THE INVENTION

The present invention will be described in further detail with reference to the examples thereof, which examples however are merely intended to be illustrative and not to be construed as limiting the scope of the invention.

EXAMPLE 1

Continuous adduct crystallization was carried out according to the process flow sheet shown in FIG. 1. In the drawing, reference numeral 1 designates a crystallization material preparation tank, 2 a crystallization tank, 3 a cooler, and 4 a circulation pump. In the equipment, the section embracing the discharge line from crystallization material preparation tank 1, crystallization tank 2, cooler 3, circulation pump and the lines connecting them (the section defined by the broken line in FIG. 1) is called the first crystallization system 5, to which a second crystallization system 6 having the same makeup as the first one 5 is connected in series. The discharge rate from circulation pump 4 was adjusted to be 800 parts by weight per minute.

Dissolution of the crystals and recrystallization were conducted using 21 parts by weight/min of the cakes of the adduct mother liquor-containing material (BPA content: 50% by weight; temperature: 50° C.) and 31 parts by weight/min of a saturated PL solution (BPA concentration: 9% by weight; temperature: 50° C.).

The whole of the said cakes was led into crystallization material preparation tank 1 through material supply line L1 while 7 parts by weight/min of the said saturated PL solution with a BPA concentration of 9% by weight was also passed into the said preparation tank 1 through crystallization mother liquor circulation line L10 to continuously and perfectly dissolve the cakes (BPA concentration: 40% by weight). The crystallization material preparation tank 1 was maintained at 94° C., equal to the saturation temperature of the PL solution with BPA concentration of 40% by weight plus 3° C. The crystallization material was perfectly liquid. It was discharged from tank 1 at a rate of 28 parts by weight per minute and continuously supplied to crystallization tank 2 through line 2 along with 800 parts by weight/min of the solution from external circulation line L4. Of the said PL solution with BPA concentration of 9% by weight, the remaining 24 parts by weight/min portion was continuously supplied to a point A of external circulation line L4 from crystallization mother liquor circulation line L9.

The flow rate to cooler 3 was controlled to maintain the outlet temperature of crystallization tank 2 at 63° C. The temperature at the inlet of the cooler (external circulation line L4) was 62.6° C. and the temperature at its outlet (point B) was 61.4° C., the temperature variance being 1.2° C. The adduct crystals were precipitated by maintaining the BPA concentration in crystallization tank 2 at 25% by weight, and the formed slurry was continuously discharged through crystallization slurry discharge line L3 at a rate of 828 parts by weight per minute.

Of this 828 parts by weight/min of the slurry discharged through slurry discharge line L3, the 52 parts by weight/min portion was supplied to second crystallization system 6 through slurry supply line L5 while the remaining 776 parts by weight/min was supplied to external circulation line L4 via circulation pump 4 along with 24 parts by weight/min of the PL solution supplied from crystallization mother liquor circulation line L9.

In the second crystallization system 6, the flow rate in its external circulation line (viz. the discharge rate of the circulation pump) was adjusted to be 800 parts by weight per minute, forming a slurry of approximately 50° C. together with 52 parts by weight/min of the slurry supplied from crystallization slurry supply line L5, and the mixed slurry was supplied to the crystallization tank at a rate of 852 parts by weight per minute and conducting crystallization, from which the slurry was released at a rate of 852 parts by weight per minute.

Of this amount (852 parts by weight per minute) of the slurry released from the crystallization tank, 800 parts by weight/min was supplied to the external circulation line and the remaining 52 parts by weight/min was supplied to solid/liquid separator 7 for separation into solids and liquid. The cakes of adduct crystals were recovered at a rate of 21 parts by weight per minute from crystal discharge line L7 of solid/liquid separator 7, and the 31 parts by weight/min mother liquor (BPA concentration: 9% by weight; temperature: 50° C.) was circulated through crystallization mother liquor discharge line L8, crystallization mother liquor circulation line L9 and line L10.

Consequently, the heat duty required in the crystallization material preparation tank 1 was approximately 23 kcal per kg of the crystal slurry after the crystallization. Also, the heat duty that had to be removed by cooler 3 was approximately 14 kcal per kg of the crystal slurry after the crystallization.

Since the temperature difference between the inlet and outlet of cooler 3 is small and limited to 1.2° C. as explained above, the load on the cooler is also small and the growth of scale on the heat transferring surface of the cooler is suppressed. Suppression of the growth of scale on the heat transferring surface was confirmed from the following fact.

In the instant example, the flow rate of cooling water to cooler 3 and the temperatures at the inlet (external circulation line L4) and the outlet (point B) of the cooler were measured continuously over a period of 4 hours, and the calculation of heat transfer was made by the following equation (1) to determine the overall heat transfer efficient U while the process side fouling factor rs1 was determined from the following equation (2). It was found that the increment of rs1 per hour was as small as 0.00008 m²K/W.

$$Q = U A \Delta T \quad (1)$$

$$1/U = 1/h1 + rs1 + Cc + rs2 + 1/h2 \quad (2)$$

wherein Q is the heat duty transferred by the coolant (cooling water), U is overall heat transfer coefficient, A is heat transferring surface area of the cooler, $\Delta T$ is logarithmic average of the temperature difference between the inlet and outlet of the cooler, h1 is heat transfer coefficient (constant) of the process side boundary film, Cc is coefficient of heat transfer resistance (a constant determined by the size of the heat transferring surface and the quality of its material), rs2 is coolant side contamination factor (constant), and h2 is coolant side boundary film heat transfer coefficient (a constant dependent on the coolant flow rate).

Incidentally, the result of the calculation conducted by using a crystallization model under the otherwise same conditions as in Example 1 showed that the degree of supersaturation at the point B of external circulation line L4 was 0.08 wt %/wt %.

COMPARATIVE EXAMPLE 1

The substantially same operations as defined in Example 1 were carried out except that the mother liquor was not circulated to the point A.

21 parts by weight/min of the cakes of the material containing the adduct crystal mother liquor (BPA content of the cakes: 50% by weight) and 31 parts by weight/min of the saturated PL solution (BPA concentration: 9% by weight; temperature: 50° C.) used as the mother liquor were wholly introduced into crystallization material preparation tank 1 and, with the BPA concentration being adjusted to be 25% by weight, the cakes were continuously and perfectly dissolved in the tank. The crystallization material was perfectly liquid. Crystallization material preparation tank 1 was maintained at the saturation temperature of the PL solution with a BPA concentration of 25% by weight plus 3° C., i.e. at 80° C. The crystallization material was discharged from its preparation tank at a rate of 52 parts by weight per minute and continuously supplied into crystallization tank 2 together with 800 parts by weight/min of the solution from external circulation line L4.

The flow rate of cooling water to cooler 3 was controlled so that the outlet temperature of crystallization tank 2 would be maintained at 63° C. The temperature at the inlet (external circulation line L4) of the cooler was 63° C. and the temperature at the outlet (point B) of cooler 3 was 61.5° C., creating a temperature difference of 1.5° C. With the BPA concentration in crystallization tank 2 being maintained at 25% by weight, the adduct crystals were precipitated and the formed slurry was continuously discharged through slurry discharge line L3 at a rate of 852 parts by weight per minute.

Of this 852 parts by weight/min slurry discharge through slurry discharge line L3, the 52 parts by weight/min portion was supplied to second crystallization system 6 through slurry supply line L5 and the remaining 800 parts by weight/min portion was supplied to external circulation line L4 via circulation pump 4.

In the second crystallization system 6, the flow rate of the slurry in its external circulation line (viz. the discharge rate of its circulation pump) was set at 800 parts by weight/min, and a slurry with a temperature of approximately 50° C. was formed together with the 52 parts by weight/min slurry supplied from slurry supply line L5. The mixed slurry was supplied to its crystallization tank at a rate of 852 parts by weight per minute and, after crystallization, discharged out at a rate of 852 parts by weight per minute. Of this 852 parts by weight/min slurry discharge from the crystallization tank, the 800 parts by weight/min portion was supplied to the external circulation line while the remaining 52 parts by weight/min portion was supplied to solid/liquid separator 7 for separation into solids and liquid. The cakes of the adduct crystals were recovered at a rate of 21 parts by weight per minute from crystal discharge line L7 of solid/liquid separator 7, and 31 parts by weight/min of the mother liquor (BPA concentration: 9% by weight; temperature: 50° C.) was circulated through mother liquor discharge line L8 and mother liquor circulation line L10.

As a result, the heat duty required in crystallization material preparation tank 1 was found to be approximately 27 kcal per kg of the crystal slurry after the crystallization, which means requirement of approximately 4 kcal/kg more heat duty than required in Example 1. Also, the heat duty that had to be removed by cooler 3 was approximately 18 kcal per kg of the crystal slurry after the crystallization, which means approximately 4 kcal/kg more heat duty must be removed than required in Example 1.

Determining the process side fouling factor rs1 by conducting the same heat transfer calculations as in Example 1, it was found that the increment of rs1 per hour was as large as 0.00015 m²K/W, which confirmed the formation of scale on the heat transferring surface.

Incidentally, the result of calculations conducted by using a crystallization model under the otherwise same conditions as in Comparative Example 1 showed that the degree of supersaturation at the point B of external circulation line L4 was 0.10 wt %/wt %.

EXAMPLE 2

Figure 2:
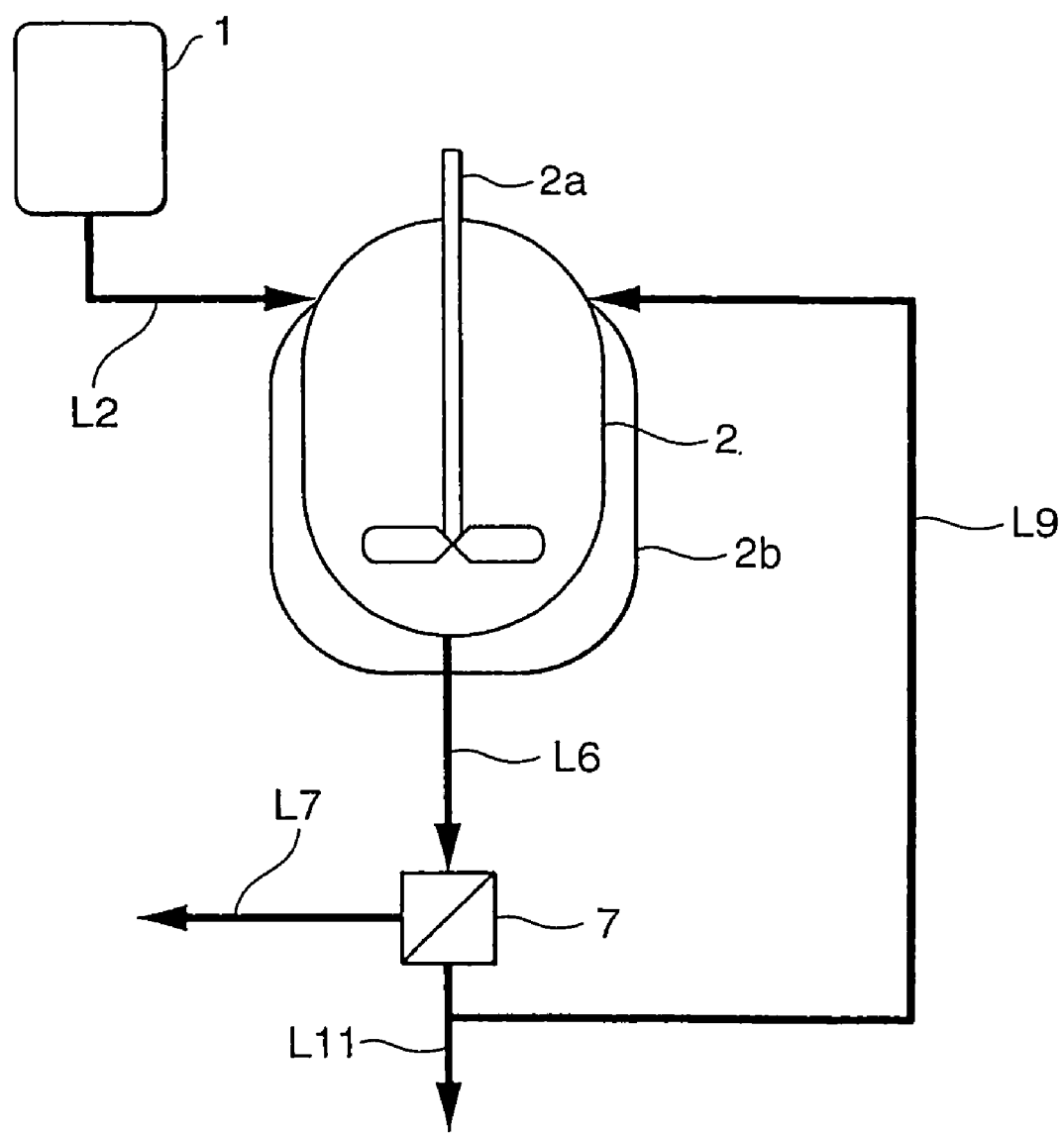
FIG. 2 is another example of process flow sheet for carrying out the process of the present invention.

Continuous crystallization of BPA was carried out according to the process flow sheet shown in FIG. 2 wherein reference numeral 2a designates an agitator and 2b a jacket.

A composition comprising 13.2% by weight of PL, 83.4% by weight of BPA, 1.7% by weight of water and 1.7% by weight of acetone was prepared in material preparation tank 1. This tank was maintained at the precipitation temperature of BPA plus 3° C., i.e. at 132° C. The prepared precipitation material was perfectly liquid. It was discharged from tank 1 at a rate of 7.2 parts by weight per minute and continuously supplied to the liquid level of crystallization tank 2 through crystallization material supply line L2.

The flow rate of the coolant to the outer jacket (2b) was controlled so that the outlet temperature of crystallization tank 2 would be maintained at 98° C. The BPA crystals were precipitated in crystallization tank 2, and the formed slurry was continuously supplied to solid/liquid separator 7 through slurry discharge line L6. The mother liquor after solid/liquid separation was circulated to crystallization tank 2 through mother liquor circulation line L9. The mother liquor was supplied to the position which was symmetrical with the supplied position of the crystallization material about the shaft of agitator 2a in crystallization tank 2.

The circulated mother liquor had a composition of 30.1 wt % PL, 62.3 wt % BPA, 3.8 wt % water and 3.8 wt % acetone and had a temperature of 98° C. Part of the mother liquor was circulated to crystallization tank 2 at a rate of 12.8 parts by weight per minute and the remainder was discharged out through mother liquor discharge line L11. Thus, the composition in circulation tank 2 was adjusted to 24 wt % PL, 70 wt % BPA, 3 wt % water and 3 wt % acetone. The slurry concentration at this point was 11% by weight, and the slurry was continuously discharged through slurry discharge line L6 at a rate of 20 parts by weight per minute. The final yield of the BPA crystals discharged from solid/liquid separator 7 was 4.1 parts by weight per minute. As a result, the heat duty to be removed by the outer jacket (2b) of crystallization tank 2 was about 10 kcal per kg of the crystal slurry after the crystallization.

COMPARATIVE EXAMPLE 2

Continuous crystallization of BPA was carried out according to the process flow sheet shown in FIG. 2, but crystallization mother liquor circulation line L9 was not used. Crystallization tank 2 in FIG. 2 is of an outer jacket type provided with an agitator in the inside.

A composition of 24 wt % PL, 70 wt % BPA, 3 wt % water and 3 wt % acetone was prepared in material preparation tank 1. This tank was maintained at the precipitation temperature of BPA plus 3° C., i.e. at 111° C. The crystallization material was perfectly liquid. The crystallization material was discharged from the tank at a rate of 20 parts by weight per minute and continuously supplied to the liquid level of crystallization tank 2 through crystallization material supply line L2. Since crystallization mother liquor circulation line L9 was not used, the composition in crystallization tank 2 was the same as that in material preparation tank 1.

The flow rate of the coolant to the outer jacket (2b) was controlled so that the outlet temperature of crystallization tank 2 would be kept at 98° C. The BPA crystals were precipitated in crystallization tank 2, and the formed slurry was continuously discharged from the tank at a rate of 20 parts by weight per minute through slurry discharge line L6. The slurry concentration was 11% by weight, and the yield of the BPA crystals released from solid/liquid separator 7 was 4.1 parts by weight per minute. The separated mother liquor was wholly discharged out through mother liquor discharge line L11. The heat duty that had to be removed by the outer jacket (2b) of crystallization tank 2 was about 11 kcal per kg of the crystal slurry after the crystallization, which means approximately 1 kcal/kg more heat duty must be removed than required in Example 2.

INDUSTRIAL APPLICABILITY

According to the present invention, the load on the cooler is reduced and the temperature difference between the inlet and outlet of the cooler is lessened, so that the degree of supersaturation is reduced to restrain the deposition of scale on the heat transferring surface. When part of the mother liquor is circulated to the crystallization step as in the present invention, its circulation rate to the crystallization material preparation step is reduced accordingly. Although the concentration of the crystallization material increases, this reduction of the circulation rate to the crystallization material preparation step leads to a corresponding decrease of the heat duty necessary for dissolving the crystallization material. The load on the cooler is also reduced. Thus, the present invention is comprehensively beneficial to the economization of energy.

What is claimed is:

1. An continuous crystallization process comprising steps of:
   (a) supplying from a crystallization material preparation tank a crystallization material containing bisphenol A to a crystallizer to form a slurry of crystals of an adduct of bisphenol A and phenol or a slurry of crystals of bisphenol A,
   (b) subjecting the slurry discharged from the crystallizer of step (a) to solid/liquid separation, and
   (c) recovering the crystals, wherein
   part of the mother liquor is circulated to the crystallizer and a ratio of an amount of mother liquor (A) circulated to the crystallizer to the amount of mother liquor (B) circulated to the crystallization material preparation tank, B/A, is not more than 5.

2. The process according to claim 1, wherein the amount of the mother liquor circulated to the crystallizer is 5 to 60% by weight of the amount of the slurry discharged.

3. The process according to claim 1, wherein the mother liquor circulated to the crystallizer contains fine crystals in a ratio of 0.01 to 10% by weight.

4. The process according to claim 1, wherein the crystallizer has an external circulation line provided with a cooler, and the mother liquor is passed into this external circulation line for circulation therethrough to the crystallizer.

5. The process according to claim 1, wherein the difference between an outlet temperature of the crystallization material preparation tank and an outlet temperature of the crystallizer is 5 to 35° C.

6. A continuous crystallization process comprising steps of:
   (a) supplying a crystallization material containing bisphenol A to a crystallizer to form a slurry of crystals of an adduct of bisphenol A and phenol or a slurry of crystals of bisphenol A,
   (b) subjecting the slurry discharged from the crystallizer of step (a) to solid/liquid separation, and
   (c) recovering the crystals, wherein part of the mother liquor is circulated to the crystallizer and the crystallizer has an external circulation line provided with a cooler, and mother liquor is passed into this external circulation line for circulation therethrough to the crystallizer.

* * * * *